US006147282A

United States Patent [19]
Goff et al.

[11] Patent Number: 6,147,282
[45] Date of Patent: Nov. 14, 2000

[54] METHOD OF CONTROLLING THE FERTILITY OF A PLANT

[75] Inventors: Stephen A. Goff, Durham; Lyle D. Crossland, Chapel Hill; Laura S. Privalle, Durham, all of N.C.

[73] Assignee: Novartis Finance Corporation, New York, N.Y.

[21] Appl. No.: 09/234,190

[22] Filed: Jan. 20, 1999

Related U.S. Application Data

[62] Division of application No. 09/010,050, Jan. 21, 1998, Pat. No. 5,880,333, which is a continuation of application No. 08/398,037, Mar. 3, 1995, abandoned.

[51] Int. Cl.$^7$ .............................. A01H 1/02; C12N 15/12; C12N 15/55; C12N 15/82
[52] U.S. Cl. ......................... 800/303; 800/271; 800/274; 800/278; 800/286; 800/287; 800/288; 435/69.7; 435/199; 435/468; 536/23.4; 536/23.5; 536/24.1; 512/2; 512/8; 512/21
[58] Field of Search ...................................... 800/271, 274, 800/278, 286, 287, 288, 303; 435/69.7, 199, 468; 536/23.4, 23.5, 24.1; 514/2, 8, 21

[56] References Cited

U.S. PATENT DOCUMENTS

| | | | |
|---|---|---|---|
| 4,833,080 | 5/1989 | Brent et al. | 435/172.3 |
| 5,262,300 | 11/1993 | Evans et al. | 435/6 |
| 5,700,650 | 12/1997 | Mak et al. | 435/7.1 |
| 5,700,682 | 12/1997 | Mak et al. | 435/252.3 |
| 5,707,798 | 1/1998 | Brann | 436/6 |
| 5,707,800 | 1/1998 | Mangelsdorf et al. | 435/6 |

FOREIGN PATENT DOCUMENTS

| | | |
|---|---|---|
| 0465024A1 | 6/1991 | European Pat. Off. . |
| 0589841A3 | 9/1993 | European Pat. Off. . |
| WO 90/08830 | 8/1990 | WIPO . |
| WO 91/12258 | 8/1991 | WIPO . |
| WO 91/13167 | 9/1991 | WIPO . |
| WO 91/14695 | 10/1991 | WIPO . |
| WO 93/03162 | 2/1993 | WIPO . |
| WO 93/09237 | 5/1993 | WIPO . |
| WO 93/21334 | 10/1993 | WIPO . |
| WO 93/23431 | 11/1993 | WIPO . |
| WO 94/01558 | 1/1994 | WIPO . |
| WO96/37609 | 11/1996 | WIPO . |

OTHER PUBLICATIONS

Evans et al. Biochem. Soc. Trans. 20:3445, 1992.
Mazzolini et al. Plant Mol. Biol. 20: 715–731, 1992.
Christopherson et al., "Ecdysteroid–dependent regulation of genes in mannalian cells by a Drosophila ecdysone receptor and chimeric transactivators", *Proc. Natl. Acad. Sci. USA*, 89:6314–6318 (1992).
Goff et al., "Identification of functional domains in the maize transcriptional activator C1: comparison of wild–type and dominant inhibitor proteins", *Genes & Development*, 5:298–309 (1991).
Henrich et al., "A steroid/thyroid hormone receptor superfamily member in *Drosophila melanogaster* that shares extensive sequence similarity with a mammalian homologue", *Nucleic Acids Research*, 18:4143–4148 (1990).
Koelle et al., "The Drosophila EcR Gene Encodes and Ecdysone Receptor, a New Member of the Steroid Receptor Superfamily", *Gene Expression Lab, Salk Institute for Biological Sudies*, 67:59–77 (1991).
Lloyd et al., "Epidermal Cell Fate Determination in Arabidopsis: Patterns Defined by a Steroid–Inducible Reglator", *Science*, 266:436–439 (1994).
Mariani et al., "Induction of male sterility in plants by a chimaeric ribonuclease gene", *Nature*, 347:737–741 (1990).
Mariani et al., "A chimaeric ribonuclease–inhibitor gene restores fertility to male sterile plants", *Nature*, 357:384–387 (1992).
Ptashne M., "How eukaryotic transcriptional activators work", *Nature*, 335:683–689 (1988).
Sadowski et al., "GAL4–VP16 is an unusually potent transcriptional activator", *Nature*, 335:563–564 (1988).
Schena et al., "A steroid–inducible gene expression system for plant cells", *Pro. Natl. Acad. Sci. USA*, 88:10421–10425 (1991).
Wing, K.D., "RH 5849, a Nonsteroidal Ecdysone Agonist: Effects on a Drosophila Cell Line", *Science*, 241:467–469 (1988).
Aoyama, et al., A glucocorticoid–mediated transcriptional induction system in transgenic plants, The Plant Journal, 11(3):605–612, 1997.

(List continued on next page.)

*Primary Examiner*—David T. Fox
*Attorney, Agent, or Firm*—J. Timothy Meigs; Gary M. Pace

[57] ABSTRACT

The present invention is drawn to a method of controlling gene expression in plants. Specifically, the method comprises obtaining a transgenic plant comprising at least two receptor expression cassettes and at least one target expression cassette. The first receptor expression cassette comprises a nucleotide sequence for a 5' regulatory region operably linked to a nucleotide sequence which encodes a first receptor polypeptide, and a 3' termination region. The second receptor expression cassette comprises a nucleotide sequence for a 5' regulatory region operably linked to a nucleotide sequence which encodes a second receptor polypeptide, and a 3' termination region. The target expression cassette comprises a nucleotide sequence for a 5' regulatory region operably linked to a nucleotide sequence which encodes a target polypeptide, and a 3' termination region, wherein the 5' regulatory region of said target expression cassette is activated by said first and second receptor polypeptides in the presence of one or more chemical ligands which are complementary to the ligand binding domain of said receptor polypeptides, whereby expression of said target polypeptide is accomplished. The method is useful for controlling various traits of agronomic importance, such as plant fertility.

33 Claims, 3 Drawing Sheets

OTHER PUBLICATIONS

Beato, Gene Regulation by Steroid, Cell 56:335–344, Feb. 10, 1989.

McNellis, et al., Glucocorticoid–inducible expression of a bacterial avirulence gene in transgenic Arabidopsis induces hypersensitive cell death, The Plant Journal, 14(2):247–257, 1998.

Martinez et al., Plant Biology '97 Final Program, Supplement to Plant Physiology, 114(3), Jul. 1997.

Tomlin, C.D.S., ed. The Pesticide Manual, Eleventh Edition, British Crop Protection Council: Surrey, UK, 1997, pp. 1147–1148.

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF43"

(iii) HYPOTHETICAL: NO (xi) SEQUENCE DESCRIPTION: SEQ ID NO:1:

CGCGGATCCT AAACAATGAA GCGGCGCTGG TCGAACAACG GC    42

(2) INFORMATION FOR SEQ ID NO:2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF23"

(iii) HYPOTHETICAL: NO (xi) SEQUENCE DESCRIPTION: SEQ ID NO:2:

CGCGGGATCC ATGCGGCCGG AATGCGTCGT CCCG    34

(2) INFORMATION FOR SEQ ID NO:3:

(i) SEQUENCE CHARACTERISTICS:
        (A) LENGTH: 30 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF42"

(iii) HYPOTHETICAL: NO (xi) SEQUENCE DESCRIPTION: SEQ ID NO:3:

CGCGGATCCA TGGACAACTG CGACCAGGAC                                30

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF37"

(iii) HYPOTHETICAL: NO (xi) SEQUENCE DESCRIPTION: SEQ ID NO:4:

GCGGGATCCC CCACCGTACT CGTCAATTC                                 29

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SA115"

(iii) HYPOTHETICAL: NO (xi) SEQUENCE DESCRIPTION: SEQ ID NO:5:

GTCGAGCTCT CGGATCCTAA AACAATGGCC CCCCCGACCG ATGTC               45

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF25"

(iii) HYPOTHETICAL: NO (xi) SEQUENCE DESCRIPTION: SEQ ID NO:6:

GATCCGACAA GGGTTCAATG CACTTGTCA                                 29

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF26"
```

```
        (iii) HYPOTHETICAL: NO (xi) SEQUENCE DESCRIPTION: SEQ ID NO:7:

GATCTGACAA GTGCATTGAA CCCTTGTCG                                         29

(2) INFORMATION FOR SEQ ID NO:8:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide SF30"

(iii) HYPOTHETICAL: NO (xi) SEQUENCE DESCRIPTION: SEQ ID NO:8:

CGCGGATCCA TGGGTCGCGA TGATCTCTCG CCTTC                                  35

(2) INFORMATION FOR SEQ ID NO:9:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE:

(iii) HYPOTHETICAL: NO (ix) FEATURE:
            (A) NAME/KEY: misc_feature
            (B) LOCATION: 1..11
            (D) OTHER INFORMATION: /note= "polylinker used to link the
                C1 transactivation domain to EcR"

(xi) SEQUENCE DESCRIPTION: SEQ ID NO:9:

VGSRSRVSSH A                                                            11

(2) INFORMATION FOR SEQ ID NO:10:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "positive strand
                oligonucleotide used to create pSKGAL2.3"

(iii) HYPOTHETICAL: NO (xi) SEQUENCE DESCRIPTION: SEQ ID NO:10:

CGGGGGATCC TAAGTAAGTA AGGTAC                                            26

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "complementary strand
                oligonucleotide used to create pSKGAL2.3"
```

-continued (iii) HYPOTHETICAL: NO (xi) SEQUENCE DESCRIPTION: SEQ ID NO:11:

CTTACTTACT TAGGATCCCC                      20

METHOD OF CONTROLLING THE FERTILITY OF A PLANT

This is a divisional of application Ser. No. 09/010,050, filed Jan. 21, 1998, now U.S. Pat. No. 5,880,333, which is a continuation of application Ser. No. 08/398,037, filed Mar. 3, 1995, abandoned.

FIELD OF THE INVENTION

The present invention relates to the chemical control of gene expression in plants. In particular, it relates to a method whereby receptor polypeptides in the presence of an appropriate chemical ligand regulate the expression of a target polypeptide in a plant cell, as well as to the expression cassettes encoding the receptor and target polypeptides and transgenic plants containing the expression cassettes.

BACKGROUND OF THE INVENTION

In some cases it is desirable to control the time or extent of expression of a phenotypic trait in plants, plant cells or plant tissue. An ideal situation would be the regulation of expression of such a trait at will, triggered by a chemical that could be easily applied to field crops, ornamental shrubs, etc. One such system of regulating gene expression which could be used to achieve this ideal situation, as yet unknown to be present naturally in plants, is the steroid and thyroid hormone superfamily of nuclear receptors.

The steroid and thyroid hormone superfamily of nuclear receptors is found in mammals and insects and is composed of over 100 known proteins. These receptors fall into at least two functionally distinct categories known as Class I and Class II. Beato, *Cell* 56: 335–344(1989); Parker, *Sem. Cancer Biol. Ser.* 1: 81–87(1990). Of the two classes, only the Class II receptors function in the nucleus as heterodimers to affect expression of target genes in the presence of hormone. The best studied examples of Class II receptor proteins are Retinoic Acid Receptor (RAR), Vitamin D Receptor (VDR), and Thyroid Hormone Receptor ($T_3R$) and Retinoic X Receptor (RXR). The receptors bind to the 5' regulatory region of the target gene and, upon binding of a chemical ligand to the receptor, the transcriptional activation (transactivation) domain of the receptor affects gene expression by interacting with other transcription initiating factors.

In addition to the Class II receptor proteins found in mammals as described above, receptors of similar structure and activity have been indentified in the insect Drosophila. Koelle et al., *Cell* 67: 59 (1991); Christianson and Kafatos, *Biochem. Biophys. Res. Comm.* 193: 1318 (1993); Henrich et al., *Nucleic Acids Res.* 18: 4143 (1990). The Ecdysone Receptor (EcR) binds the steroid hormone 20-hydroxyecdysone and, when heterodimerized with the product of the Ultraspiracle gene (USP), will transactivate gene expression. USP is most homologous to RXRα, and RXR is capable of forming heterodimers with EcR. Thomas et al., *Nature* 362: 471–475 (1993). Additional chemical ligands besides 20-hydroxyecdysone, such as other hormone agonists or antagonists, will also bind to these receptors and cause transactivation of a target gene.

One member of the steroid and thyroid superfamily of nuclear receptors, the Class I Glucocorticoid Receptor (GR) which utilizes chaperonins and does not function by heterodimerization with other receptors, has been shown to transactivate a target gene in plant cells. Schena et al., *Proc. Natl. Acad Sci. USA* 88: 10421–10425 (1991). A fragment containing the ligand binding domain from GR was fused to the anthocyanin regulatory protein known as 'R' and shown to stimulate production of anthocyanin in transgenic *Arabidopsis thaliana* in response to the application of the appropriate chemical ligand. Lloyd et al., *Science* 226: 436 (1994). It was also reported by Lloyd et al. that full-length GR did not activate gene expression in stably transformed *Arabidopsis thaliana* whereas it did in transient assays in tobacco protoplasts. Furthermore, fusions of R with a fragment from the Estrogen Receptor (ER), another Class I receptor which utilizes chaperonins, also stimulated production of anthocyanin in the presence of the appropriate chemical ligand but showed 'substantial' background expression.

The distinguishing feature of the Class II receptor proteins, transactivation of a target gene by heterodimerized receptors in the presence of an appropriate chemical ligand, offer previously unrecognized opportunities for chemical control of gene expression in plants. The use of heterodimers allows a broader range of gene control strategies, and chemicals are already known for agricultural use which can trigger receptor-mediated transactivation of target gene expression of this class. Furthermore, gene control strategies for plants which utilize nuclear receptors that do not occur naturally in plants have the attractive feature of inducing only the genetically engineered target gene. The class II receptors in general, however, possess fairly poor transcriptional activation domains, and the ability of the receptors to transactivate target genes may be enhanced by the addition of other transcriptional activation domains, particularly from plant or viral species. Further modification would also be needed in order to provide minimum basal activity which increases rapidly to high levels in the presence of a triggering chemical. As has been demonstrated by the present invention, receptor polypeptides based on the class II model, and the genes that encode them, have been developed which function in plant cells to control expression of a target polypeptide wherein the receptor polypeptides activate the 5' regulatory region of a target expression cassette in the presence of a chemical ligand. Such a method of controlling gene expression in plants would be useful for controlling various traits of agronomic importance, such as plant fertility.

SUMMARY OF THE INVENTION

The present invention is drawn to a method of controlling gene expression in plants. Specifically, the method comprises transforming a plant with at least two receptor expression cassettes and at least one target expression cassette. The first receptor expression cassette comprises a nucleotide sequence for a 5' regulatory region operably linked to a nucleotide sequence which encodes a first receptor polypeptide operably linked to a 3' termination region. The second receptor expression cassette comprises a nucleotide sequence for a 5' regulatory region operably linked to a nucleotide sequence which encodes a second receptor polypeptide operably linked to a 3' termination region. The first and second receptor polypeptides comprise a first and second ligand binding domain, respectively, which are mutually distinct. The target expression cassette comprises a nucleotide sequence for a 5' regulatory region operably linked to a nucleotide sequence which encodes a target polypeptide operably linked to a 3' termination region, wherein the 5' regulatory region of said target expression cassette is activated by said first and second receptor polypeptides in the presence of one or more chemical ligands, whereby expression of said target polypeptide is accomplished. The method is useful for controlling various traits of agronomic importance, such as plant fertility.

The invention is further drawn to transgenic plants comprising a first and second receptor expression cassette and a target expression cassette. Also encompassed by the invention are receptor expression cassettes and target receptor cassettes capable of high level expression in plants.

The receptor polypeptides comprise a ligand binding domain, DNA binding domain and a transactivation domain. Further, the receptor polypeptides may have a chimeric form, where one or more of the ligand binding, DNA binding or transactivation domains are obtained from a source heterologous with respect to other domains present in the chimeric receptor polypeptide.

DETAILED DESCRIPTION OF THE INVENTION

Definitons and Nomenclature

Figure 1:
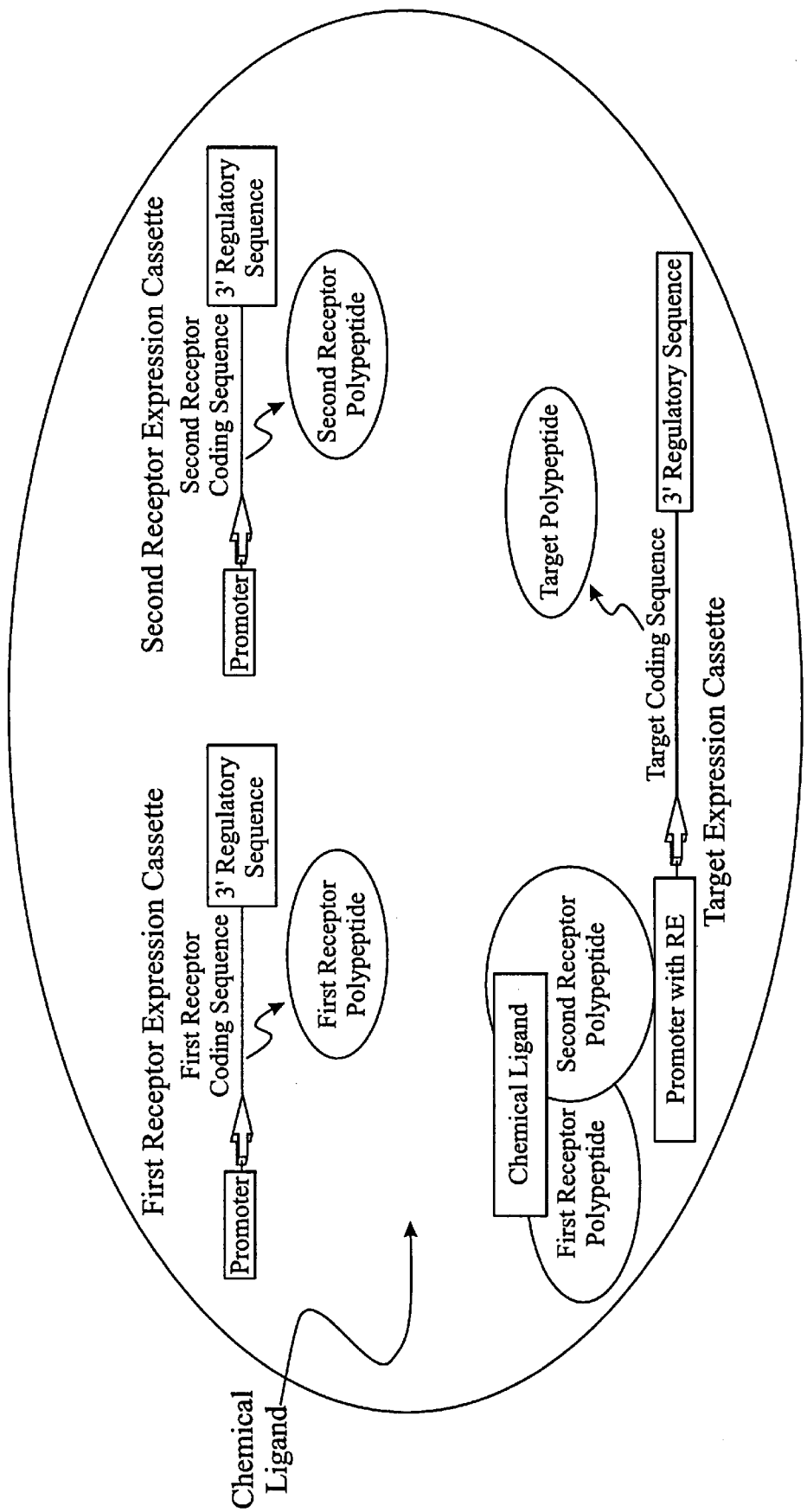
FIG. 1. Pictoral representation of a plant cell comprising a first receptor expression cassette which encodes a first receptor polypeptide comprising a first ligand binding domain, and a second receptor expression cassette encoding a second receptor polypeptide comprising a second ligand binding domain. The first and second receptor polypeptides are mutually distinct. The plant cell further comprises a target expression cassette which encodes a target polypeptide, wherein the target polypeptide is expressed upon activation of the 5' regulatory region of the target expression cassette by the first and second receptor polypeptides in the presence of a chemical ligand which is complementary to said first or second ligand binding domain.

"Receptor polypeptide" as used herein refers to polypeptides which activate the expression of a target polypeptide in response to an applied chemical ligand. The receptor polypeptide is comprised of a ligand binding domain, a DNA binding domain and a transactivation domain. A "receptor expression cassette" comprises a nucleotide sequence for a 5' regulatory region operably linked to a nucleotide sequence which encodes a receptor polypeptide and an untranslated 3' termination region (stop codon and polyadenylation sequence).

The ligand binding domain comprises a sequence of amino acids whose structure binds non-covalently a complementary chemical ligand. Hence, a ligand binding domain and its chemical ligand form a complementary binding pair.

The DNA binding domain comprises a sequence of amino acids which binds non-covalently a specific nucleotide sequence known as a response element (RE). The response elements are located in the 5' regulatory region of the target expression cassette and comprise a pair of half-sites, each half-site having a 6 base pair core where a single DNA binding domain recognizes a single half-site. The half-sites may be arranged in relative linear orientation to each other as either direct repeats, palindromic repeats or inverted repeats. A response element binds either a homodimer or heterodimer of receptor polypeptides. The nucleotide sequence and linear orientation of the half-sites determines which DNA binding domain or DNA binding domains will form a complementary binding pair with said response element, as well as the ability of receptor polypeptides to interact with each other in a dimer.

The transactivation domain comprises one or more sequences of amino acids acting as subdomains which affect the operation of transcription factors during preinitiation and assembly at the TATA box. The effect of the transactivation domain is to allow repeated transcription initiation events, leading to greater levels of gene expression.

A "moiety" refers to that share or portion of a receptor polypeptide that is derived from the indicated source. For example, "EcR-moiety" refers to that portion of the receptor polypeptide that was derived from the native ecdysone receptor. Moiety as used here may comprise one or more domains.

"Homologous" is used to indicate that a receptor polypeptide has the same natural origin with respect to its current host. For example, the ecdysone receptor (EcR) is found in certain insect species and is said to be homologous with respect to the insect species in which it originates. "Homologous" is also used to indicate that one or more of the domains, present in a receptor polypeptide have the same natural origin with respect to each other. For example, the DNA binding domain and the ligand binding domain of EcR are considered to be of a homologous origin with respect to each other.

"Heterologous" is used to indicate that a receptor polypeptide has a different natural origin with respect to its current host. For example, if the ecdysone receptor (EcR) from an insect species is expressed in a plant cell, then the EcR is described as being heterologous with respect to its current host, which is the plant cell. "Heterologous" is also used to indicate that one or more of the domains present in a receptor polypeptide differ in their natural origin with respect to other domains present. For example, if the transactivation domain from the herpes simplex VP16 protein is fused to the USP receptor from Drosophila, then the VP16 transactivation domain is heterologous with respect to the USP-moiety. Furthermore, if a domain from USP is fused to a domain from RXR to make a functional receptor, then the chimeric fusion would have domains that are heterlogous to each other. In addition, a heterologous receptor polypeptide comprising the fusion of a VP16 transactivation domain and a USP-moiety, when expressed in a plant, would also be considered heterologous with respect to the plant host.

The term "chimeric" is used to indicate that the receptor polypeptide is comprised of domains at least one of which has an origin that is heterologous with respect to the other domains present. These chimeric receptor polypeptides are encoded by nucleotide sequences which have been fused or ligated together resulting in a coding sequence which does not occur naturally.

The chimeric receptor polypeptides of the present invention are referenced by a linear nomenclature from N-terminal to C-terminal portion of the polypeptide. Using this nomenclature, a chimeric receptor polypeptide having the transactivation domain from VP16 fused to the N-terminal end of the USP receptor would be designated as VP16-USP. Conversely, if VP16 was fused to the C-terminus of the USP receptor the chimeric receptor polypeptide would be designated USP-VP16.

Gene constructions are denominated in terms of a 5' regulatory region and its operably-linked coding sequence, where the 5' regulatory region is designated before a slash mark (/) and the coding sequence designated after the slash mark. For example, the gene construction 35S/USP-VP16 designates the 35S promoter of Cauliflower Mosaic Virus fused to the chimeric receptor USP-VP16, where the transactivation domain of VP16 is fused to the C-terminal end of USP.

A "target expression cassette" comprises a nucleotide sequence for a 5' regulatory region operably linked to a nucleotide sequence which encodes a target polypeptide whose expression is activated by the receptor polypeptides in the presence of a chemical ligand. The 5' regulatory region of the target gene comprises a core promoter sequence, an initiation of transcription sequence and the response element or response elements necessary for complementary binding of the receptor polypeptides. The target expression cassette also possesses a 3' termination region (stop codon and polyadenylation sequence).

Native and Chimeric Receptor Polypeptides for Controlling Gene Expression in Plants The method of the present invention comprises expressing within a plant at least two receptor polypeptides which, in the presence of one or more chemical ligands, activate the 5' regulatory region of a target expression cassette within a transgenic plant (FIG. 1). At least two receptor polypeptides are required to activate the 5' regulatory region. These two receptor polypeptides form a dimer. When the two receptor polypeptides are identical they form a "homodimer" and when the two receptor polypeptides are different they form a "heterodimer." One or both of the two receptor polypeptides present in a homodimer or heterodimer may be in a chimeric form, as described below. Examples of heterodimers encompassed by the invention include, but are not limited to, ECR+USP, ECR+RXR or chimeric forms thereof.

The receptor polypeptides are composed of a ligand binding domain, a DNA binding domain and a transactivation domain. The DNA binding domain binds the receptor polypeptide to the 5' regulatory region of the target expression cassette at the site of the response element. The ligand binding domain of the receptor polypeptides binds, when present, the complementary chemical ligand. Binding of the chemical ligand causes a conformational change in the receptor polypeptide and allows the transactivation domain to affect transcription of the coding sequence of the target expression cassette, resulting in production of the target polypeptide.

The chimeric receptor polypeptides used in the present invention have one or more domains obtained from a heterologous source. The use of chimeric receptor polypeptides has the benefit of combining domains from different sources, thus providing a receptor polypeptide activated by a choice of chemical ligands and possessing superior ligand binding, DNA binding and transactivation characteristics. One preferred embodiment of the present invention are chimeric receptor polypeptides where the complementary chemical ligand is selected from an insecticide, an insect hormone, or antagonists or agonists of insect hormones.

The 5' regulatory region of the receptor expression cassettes further comprises a promoter which permits expression in plant tissues and cells. Appropriate promoters are chosen for the receptor expression cassettes so that expression of the receptor polypeptides may be constitutive, developmentally regulated, tissue specific, cell specific or cell compartment specific. Promoters may also be chosen so that expression of the receptor polypeptides themselves can be chemically-induced in the plant, thereby increasing the level of promoter induction by ligand. By combining promoter elements which confer specific expression with those conferring chemically-induced expression, the receptor polypeptides may be expressed or activated within specific cells or tissues of the plant in response to chemical application. The nucleotide sequence which encodes the receptor polypeptide may be modified for improved expression in plants, improved functionality, or both. Such modifications include, but are not limited to, altering codon usage, insertion of introns or creation of mutations. In one embodiment of the invention, expression cassettes comprising an anther-specific or pistil-specific promoter operably linked to a nucleotide sequence which encodes a chimeric receptor polypeptide are used to activate the expression of a target polypeptide.

Target polypeptides whose expression is activated by the receptor polypeptides in the presence of a chemical ligand are also disclosed. The expression of any coding sequence may be controlled by the present invention, provided that the promoter operably linked to said coding sequence has been engineered to contain the response element or response elements which are complementary to the DNA binding domain of the receptor polypeptides used. For example, target polypeptides which are useful for controlling plant fertility are activated by the receptor polypeptides in the presence of a chemical ligand.

Selecting Domains for Use in a Chimeric Receptor Polypeptide

Chimeric receptor polypeptides may be used in the present invention to activate expression of a target polypeptide. One or more of the three domains of a receptor polypeptide may be chosen from a heterologous source based upon their effectiveness for transactivation, DNA binding or chemical ligand binding. The domains of the chimeric receptor polypeptide may also be obtained from any organism, such as plants, insects and mammals which have similar transcriptional regulating functions. In one embodiment of the invention, these domains are selected from other members the steroid and thyroid hormone superfamily of nuclear receptors. Chimeric receptor polypeptides as provided herein offer the advantage of combining optimum transactivating activity, complementary binding of a selected chemical ligand and recognition of a specific response element. Thus, a chimeric polypeptide may be constructed that is tailored for a specific purpose. These chimeric receptor polypeptides also provide improved functionality in the heterologous environment of a plant cell.

It is also considered a part of the present invention that the transactivation, ligand-binding and DNA-binding domains may be assembled in the chimeric receptor polypeptide in any functional arrangement. For example, where one subdomain of a transactivation domain is found at the N-terminal portion of a naturally-occuring receptor, the chimeric receptor polypeptide of the present invention may include a transactivation subdomain at the C-terminus in place of, or in addition to, a subdomain at the N-terminus. Chimeric receptor polypeptides as disclosed herein may also have multiple domains of the same type, for example, more than one transactivation domain (or two subdomains) per receptor polypeptide.

The Ligand Binding Domain

The ligand binding domain of the receptor polypeptide provides the means by which the 5' regulatory region of the target expression cassette is activated in response to the presence of a chemical ligand. The ecdysone receptor (EcR) from Drosophila is one example of a receptor polypeptide where complementary chemical ligands have been identified which bind to the ligand binding domain. The steroid hormone ecdysone triggers coordinate changes in tissue development that results in metamorphosis, and ecdysone has been shown to bind to EcR. Koelle et al. *Cell* 67: 59–77, 1991. The plant-produced analog of ecdysone, muristerone, also binds to the ligand binding domain of EcR. Other chemicals, such as the non-steroidal ecdysone agonists RH 5849 (Wing, *Science* 241: 467–469 (1988)) and RH 5992, the latter known as the insecticide MIMIC®, also will act as a chemical ligand for the ligand binding domain of EcR. The EcR and its ligand binding domain have been found in the present invention to be particularly useful for controlling target polypeptide expression in plant cells, as described in the examples below.

Another receptor from Drosophila, Ultraspiracle (USP), also known as "2C", has been isolated and cloned, and its ligand binding domain domain has been identified. (Henrich et al., *Nucleic Acids Research* 18: 4143–4148 (1990)). USP is most similar to the steroid receptor RXRα, which has as a chemical ligand 9-cis-retinoic acid. USP has also been shown to form a heterodimer with EcR and regulate the expression of a target polypeptide in transformed mice kidney cells in response to the application of ecdysone. (Evans et al. WO 94/01558). The receptor USP and its ligand binding domain have been found in the present invention to be particularly useful for controlling target polypeptide expression in plants, as described in the examples below.

Ligand binding domains for the construction of chimeric receptor polypeptides may also be obtained from a variety of other sources. Particularly useful sources of ligand binding domains include but are not limited to Class II receptor proteins of the steroid and thyroid hormone superfamily of nuclear receptors.

The choice of chemical ligand will depend on which ligand binding domains are present in the receptor polypeptide. Any chemical compound will suffice as long as it is shown to form a complementary binding pair with the chosen ligand binding domain. When a naturally-occurring compound is known to form a complementary binding pair with a particular ligand binding domain, these known compounds also find use in the present invention. Particularly useful sources of ligand binding domains include but are not limited to Class II receptor proteins of the steroid and thyroid hormone superfamily of nuclear receptors. Particularly useful chemicals include but are not limited to insecticides which form a complementary binding pair with the ligand binding domain. Such chemicals include but are not limited to hormones, hormone agonists or hormone antagonists whose function as insecticides can be acscribed to their binding to native receptor proteins in insects. In addition, chemicals with these hormone or hormone-related properties which are known as insecticides have the additional benefit of already being examined for agricultural production, making such chemicals "ready-to-use" for field application to crops. Useful chemicals with these properties include but are not limited to fenoxycarb, CGA 59,205, MIMIC®, and RH 5849.

The invention also encompasses ways of reducing background so that induction is large relative to the suppressed background expression. Many ligand binding domains will form a complementary binding pair with more than one chemical ligand. In some cases, these chemical ligands will bind but have no known function. In other cases, there may be chemical ligands endogenous to the current host in which the receptor polypeptides are expressed which will bind to the ligand binding domain. In order to avoid endogenous chemical ligands in a heterologous host from binding with the expressed receptor polypeptides and unintentionally affecting expression of the target gene, it may be desirable to mutate the coding sequence for the receptor polypeptide so that it recognizes only the chemical ligand applied exogenously. Useful methods of mutagenesis are known in the art, such as chemical mutagenesis or site-directed mutagenesis.

In one method, mutant receptor polypeptides are prepared by PCR mutagenesis of the nucelotide sequence encoding the ligand binding domain of EcR or USP. These mutant receptor polypeptides are expressed in a host organism that lends itself to convenient screening and isolation techniques, such as yeast. Screening for mutant receptor polypeptides that exhibit decreased basal activity and a greater fold induction in such a host organism will, however, only provide candidates for further testing in plant cells, since it is clear from work with the glucocorticoid receptor (GR) that although receptors from the steroid and thyroid hormone superfamily can function in yeast, it is not predictive of functionality in transgenic plants (Lloyd et al., *Science* 226: 436 (1994)). Further limiting the application of results from yeast is the observation that yeast cells which express GR do not respond to the commonly used chemical ligand dexamethasone, while this ligand is functional in other heterologous systems (Schena et al, *Proc. Natl. Acad Sci USA* 88: 10421–10425 (1991)).

Further testing in plant cells is accomplished by preparing receptor expression cassettes which encode the mutated receptor polypeptides and transforming them into plant cells in combination with a target expression cassette. The transformed plant cells are tested for activation of the 5'-regulatory region of the target expression cassette by the mutant receptor polypeptides in the presence of an appropriate chemical ligand. Mutant receptor polypeptides which produce low basal expression of a target polypeptide in the absence of chemical ligand and high expression of target polypeptide in the presence of an appropriate chemical ligand are useful for controlling gene expression in plants.

Furthermore, heterodimerization in the absence of ligand can also result in unintentional activation of the 5' regulatory region of the target expression cassette, thereby producing high levels of basal expression of the target polypeptide. Another region of the ligand binding domain known as the heptad repeat region is thought to influence the degree of heterodimerization in the absence of ligand. (Au-Fliegner et al., *Mol. Cell. Biol.* 13: 5725 (1993)). In one embodiment of the present invention, the ninth heptad repeat of the heptad repeat region is mutated using site directed PCR mutagenesis in such a way as to alter the interaction between subunits of the receptor polypeptide heterodimers in the absence of chemical ligand.

The DNA Binding Domain and Its Response Elements

The DNA binding domain is a sequence of amino acids which has certain functional features which are responsible for binding of the receptor polypeptide to a specific sequence of nucleotides, the response elements, present in the 5' regulatory region of the target expression cassette. In one embodiment of the invention, the DNA binding domain is obtained from a Class II nuclear receptor and contains cysteine residues arranged in such a way that, when coordinated by zinc ions, forms the so-called "zinc-finger" motif. The structure of DNA binding domains for the Class II nuclear receptors is highly conserved from one species to another, and consequently there is limited variation in the response elements used to form a complementary binding pair. (Evans, *Science* 240: 889–895 (1988)). Nevertheless, considerable flexibility can be introduced into the method of controlling gene expression by using these conserved response elements in other ways. In a preferred embodiment of the invention, multiple copies of the appropriate response element are placed in the 5' regulatory region, which allows multiple sites for binding of receptor polypeptide heterodimers resulting in a greater degree of activation.

Further flexibility in the gene control method can be achieved by changing the linear orientation or position of the response elements in the 5' regulatory region. The response elements which are recognized by Class II receptor proteins have a "dyad" symmetry, consistent with their functioning with dimerized receptor polypeptides to control gene expression. (Evans, *Science* 240: 889–895 (1988)). Hence, a receptor polypeptide dimer binds to a "whole-site," with each receptor polypeptide individually binding to a "half-site." Furthermore, these "half-sites" may be oriented in either a direct repeat, inverted repeat or palindromic fashion. The EcR and USP native receptor polypeptides recognize a palindromic response element, unlike most class II receptor proteins which recognize direct repeat response elements with appropriate spacing.

Additional flexibility in controlling gene expression by the present invention may be obtained by using DNA binding domains and response elements from other transcriptional activators, which include but is not limited to the lexA or GAL4 proteins. The DNA binding domain from the LexA protein encoded by the lexA gene from *E. coli* and its complementary binding site (Brent and Ptashne, *Cell* 43:729–736, (1985), which describes a LexA/GAL4 transcriptional activator) can be utilized. The GAL4 protein of yeast (Sadowski et al. *Nature* 335: 563–564 (1988), which describes a GAL4-VP16 transcriptional activator). In one preferred embodiment of the invention, a chimeric receptor polypeptide is constructed by fusing the GAL4 DNA binding domain to a moiety containing the ligand binding domain from EcR which, when heterodimerized with USP or a USP-moiety, can control expression of a target polypeptide.

Yet a further degree of flexibility in controlling gene expression can be obtained by combining response elements which form complementary binding pairs with DNA binding domains from different types of transcriptional activators, i.e., using overlapping response elements from GAL4 and a member of the steroid and thyroid hormone superfamily of nuclear receptors. One example is the 5' regulatory region of a target expression cassette which comprises the response element from GAL4 and overlaps with the response element of $T_3R$. When $T_3R$ proteins homodimerize in the absence of chemical ligand, they will recognize their own response element and bind to it, thereby blocking the adjacent response element for GAL4. There is no activation of the 5' regulatory region of the target expression cassette in this situation. Upon addition of a complementary ligand for $T_3R$, the homodimer is separated and released from its response element, unmasking the adjacent response element for GAL4. Once unmasked, the chimeric receptor polypeptides utilizing the DNA binding domain from GAL4 may bind to the response element under appropriate dimerization conditions and thereby activate expression of the target polypeptide.

The Transactivation Domain

Transactivation domains can be defined as amino acid sequences that, when combined with the DNA binding domain in a receptor polypeptide, increase productive transcription initiation by RNA polymerases. (See generally Ptashne, *Nature* 335: 683–689 (1988)). Different transactivation domains are known to have different degrees of effectiveness in their ability to increase transcription initiation. In the present invention it is desirable to use transactivation domains which have superior transactivating effectiveness in plant cells in order to create a high level of target polypeptide expression in response to the presence of chemical ligand. Transactivation domains which have been shown to be particularly effective in the method of the present invention include but are not limited to VP16 (isolated from the herpes simplex virus) and C1 (isolated from maize). In one preferred embodiment of the present invention, the transactivation domain from VP16 is fused to a USP-moiety for use as one monomer of a receptor polypeptide heterodimer for controlling target polypeptide expression in plants. A further preferred embodiment is the fusion of the transactivation domain from C1 to a EcR-moiety as a monomer. Other transactivation domains may also be effective.

Repression of Gene Expression

As described above, the method of the present invention can be used to increase gene expression over a minimal, basal level. One of the outstanding benefits of the present method, however, is that it can also be used for decreasing or inhibiting gene expression, i.e., gene repression. Repression can be achieved by the formation of homodimers where the half-sites of the response element have an linear orientation distinct from the linear orientation which permits heterodimer binding. Under these conditions, homodimers bound to the 5' regulatory region of the target expression cassette repress gene expression since they interfere with the transcription process. Hence, gene repression can be accomplished by inclusion in the 5' regulatory region an response element or response elements which permit homodimer binding. In one embodiment of the invention, gene repression is achieved by binding of a homodimer of USP or EcR to the 5' regulatory region of a target expression cassette which comprises a complementary direct repeat half-site.

Gene repression caused by homodimer binding would be released by addition of a chemical ligand which triggers heterodimerization. This heterodimerization then activates the 5' regulatory region of the target expression cassette. For example, in a transgenic plant expressing USP and EcR receptor polypeptides and comprising a target expression cassette having both a palindrome half site response element and a direct repeat (or inverted repeat) half site response element complementary to the DNA binding domain of USP and EcR, the expression of the target polypeptide will be repressed. In the presence of RH 5992, or other chemical ligand which binds to the ligand binding domain of EcR or USP, or both, heterodimerization with USP and consequent binding to the other response element present occurs, which in turn leads to activation of the 5' regulatory region of the target expression cassette. Thus, repression of the target expression cassette would be released.

Controlling Gene Expression in Plants

For expression in plants, suitable promoters must be chosen for both the receptor expression cassettes and the target expression cassette. Unless specifically noted, the promoters discussed below may be used to direct expression in plants of either the receptor polypeptides or the target polypeptide. These promoters include, but are not limited to, constitutive, inducible, temporally regulated, developmentally regulated, chemically regulated, tissue-preferred and tissue-specific promoters. Preferred constitutive promoters include but are not limited to the CAMV 35S and 19S promoters (U.S. Pat. No. 5,352,605). Additionally preferred promoters include but are not limited to one of several of the actin genes, which are known to be expressed in most cell types. The promoter described by McElroy et al., *Mol. Gen. Genet.* 231: 150–160 (1991), can be easily incorporated into the receptor expression cassettes of the present invention and are particularly suitable for use in monocotyledonous hosts. Yet another preferred constitutive promoter is derived from ubiquitin, which is another gene product known to accumulate in many cell types. The ubiquitin promoter has been cloned from several species for use in transgenic plants (e.g. sunflower—Binet et al., *Plant Science* 79: 87–94 (1991); maize— Christensen et al., *Plant Molec. Biol.* 12: 619–632 (1989)). The maize ubiquitin promoter has been developed in transgenic monocot systems and its sequence and vectors constructed for transformation of monocotyledonous plants are disclosed in patent publication EP 0 342 926. The ubiquitin promoter is suitable for use in the present invention in transgenic plants, especially monocotyledons. Further useful promoters are the U2 and U5 snRNA promoters from maize (Brown et al., *Nucleic Acids Res.* 17: 8991 (1989)) and the promoter from alcohol dehydrogenase (Dennis et al., *Nucleic Acids Res.* 12: 3983 (1984)) Tissue-specific or tissue-preferential promoters useful in the present invention in plants, particularly maize, are those which direct expression in root, pith, leaf or pollen. Such promoters are disclosed in U.S. Ser. No. 07/951,715, now U.S. Pat. No. 5,625,136, herein incorporated by reference in its entirety. Also useful are promoters which confer seed-specific expression, such as those disclosed by Schermthaner et al., *EMBO J.* 7: 1249 (1988); anther-specific promoters ant32 and ant43D disclosed in U.S. Ser. No. 07/908,242, now abandoned, herein incorporated by reference in its entirety; anther (tapetal) specific promoter B6 (Huffman et al., *J. Cell. Biochem.* 17B: Abstract #D209 (1993)); pistil-specific promoters such as a modified S13 promoter (Dzelkalns et al., *Plant Cell* 5:855 (1993)).

Also useful in the present invention are chemically-induced promoters. Particular promoters in this category useful for directing the expression of the receptor polypeptides or target polypeptide in plants are disclosed, for example, in U.S. Ser. No. 08/181,271, now U.S. Pat. No. 5,614,395, herein incorporated by reference in its entirety.

The 5' regulatory region of either the receptor expression cassette or the target expression cassette may also include other enhancing sequences. Numerous sequences have been found to enhance gene expression in transgenic plants. For example, a number of non-translated leader sequences derived from viruses are known to enhance expression. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990)). Other leaders known in the art include but are not limited to:

Picornavirus leaders, for example, EMCV leader (Encephalomyocarditis 5' noncoding region) (Elroy-Stein, O., Fuerst, T. R., and Moss, B. *PNAS USA* 86:6126–6130 (1989));

Potyvirus leaders, for example, TEV leader (Tobacco Etch Virus) (Allison et al., (1986); MDMV leader (Maize Dwarf Mosaic Virus); *Virology*, 154:9–20);

Human immunoglobulin heavy-chain binding protein (BiP) leader, (Macejak, D. G., and Sarnow, P., *Nature*, 353: 90–94 (1991);

Untranslated leader from the coat protein mRNA of alfalfa mosaic virus (AMV RNA 4), (Jobling, S. A., and Gehrke, L., *Nature*, 325:622–625 (1987);

Tobacco mosaic virus leader (TMV), (Gallie, D.R. et al., *Molecular Biology of RNA*, pages 237–256 (1989); and Maize Chlorotic Mottle Virus leader (MCMV) (Lommel, S. A. et al., *Virology*, 81:382–385 (1991). See also, Della-Cioppa et al., *Plant Physiology*, 84:965–968 (1987).

Various intron sequences have been shown to enhance expression when added to the 5' regulatory region, particularly in monocotyledonous cells. For example, the introns of the maize Adh1 gene have been found to significantly enhance the expression of the wild-type gene under its cognate promoter when introduced into maize cells (Callis et al., *Genes Develep* 1: 1183–1200 (1987)).

In addition to promoters, a variety of 3' transcriptional terminators are also available for use in the present invention. Transcriptional terminators are responsible for the termination of transcription and correct mRNA polyadenylation. Appropriate transcriptional terminators and those which are known to function in plants include the CaMV 35S terminator, the tml terminator, the nopaline synthase terminator, the pea rbcS E9 terminator and others known in the art. These can be used in both monocotyledons and dicotyledons.

In addition to incorporating one or more of the aforementioned elements into the 5' regulatory region of a target expression cassette, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter which is obtained from the bronze 1 gene of maize. The Bz1 core promoter was obtained from the "myc" mutant Bz1-luciferase construct pBz1LucR98 via cleavage at the NheI site located at –53 to –58. Roth et al., *Plant Cell* 3: 317 (1991). The derived Bz1 core promoter fragment thus extends from –53 to +227 and includes the Bz1 intron-1 in the 5' untranslated region.

Plant Transformation

The expression cassettes of the present invention can be introduced into the plant cell in a number of art-recognized ways. Those skilled in the art will appreciate that the choice of method might depend on the type of plant, i.e. monocotyledonous or dicotyledonous, targeted for transformation. Suitable methods of transforming plant cells include, but are not limited to, microinjection (Crossway et al., *BioTechniques* 4:320–334 (1986)), electroporation (Riggs et al., *Proc. Natl. Acad. Sci. USA* 83:5602–5606 (1986), Agrobacterium-mediated transformation (Hinchee et al., *Biotechnology* 6:915–921 (1988)), direct gene transfer (Paszkowski et al., *EMBO J.* 3:2717–2722 (1984)), and ballistic particle acceleration using devices available from Agracetus, Inc., Madison, Wisconsin and BioRad, Hercules, Calif. (see, for example, Sanford et al., U.S. Pat. No. 4,945,050; and McCabe et al., *Biotechnology* 6:923–926 (1988)). Also see, Weissinger et al., *Annual Rev. Genet.* 22:421–477 (1988); Sanford et al., *Particulate Science and Technology* 5:27–37 (1987)(onion); Christou et al., *Plant Physiol.* 87:671–674 (1988)(soybean); McCabe et al., *Bio/Technology* 6:923–926 (1988)(soybean); Datta et al., *Bio/Technology* 8:736–740 (1990)(rice); Klein et al., *Proc. Natl. Acad. Sci. USA,* 85:43054309 (1988)(maize); Klein et al., *Bio/Technology* 6:559–563 (1988)(maize); Klein et al., *Plant Physiol.* 91:440–444 (1988)(maize); Fromm et al., *Bio/Technology* 8:833–839 (1990)(maize); and Gordon-Kamm et al., *Plant Cell* 2:603–618 (1990)(maize); Svab et al., *Proc. Natl. Acad. Sci. USA* 87: 8526–8530 (1990) (tobacco chloroplast); Koziel et al., *Biotechnology* 11: 194–200 (1993)(maize); Shimamoto et al., *Nature* 338: 274–277 (1989)(rice); Christou et al., *Biotechnology* 9: 957–962 (1991)(rice); European Patent Application EP 0 332 581 (orchardgrass and other Pooideae); Vasil et al., Biotechnology 11: 1553–1558 (1993)(wheat); Weeks et al., Plant Physiol. 102: 1077–1084 (1993)(wheat).

One particularly preferred set of embodiments for the introduction of the expression cassettes of the present invention into maize by microprojectile bombardment is described in U.S. Ser. No. 08/008,374, now abandoned, herein incorporated by reference in its entirety. An additional preferred embodiment is the protoplast transformation method for maize as disclosed in European Patent Application EP 0 292 435, as well as in U.S. Ser. No. 08/024,875, now U.S. Pat. No. 5,350,687, hereby incorporated by reference in its entirety. One particularly preferred set of embodiments for the introduction of the expression cassettes of the present invention into wheat by microprojectile bombardment can be found in U.S. Ser. No. 08/147,161, now abandoned, herein incorporated by reference in its entirety.

Transformation of plants can be undertaken with a single DNA molecule or multiple DNA molecules (ie. co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

Many vectors are available for transformation using *Agrobacterium tumefaciens*. These a typically carry at least one T-DNA border sequence and include vectors such as pBIN19 (Bevan, *Nucl. Acids Res.* (1984)). In one preferred embodiment, the expression cassettes of the present invention may be inserted into either of the binary vectors pCIB200 and pCIB2001 for use with Agrobacterium. These vector cassettes for Agrobacterium-mediated transformation wear constructed in the following manner. pTJS75kan was created by NarI digestion of pTJS75 (Schmidhauser & Helinski, *J. Bacteriol.* 164: 446455 (1985)) allowing excision of the tetracycline-resistance gene, followed by insertion of an AccI fragment from pUC4K carrying an NPTII (Messing & Vierra, *Gene* 19: 259–268 (1982); Bevan et al., *Nature* 304: 184–187 (1983); McBride et al., Plant Molecular Biology 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., *Gene* 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. The plasmid pCEB2001 is a derivative of pCIB200 which was created by the insertion into the polylinker of additional restriction sites. Unique restriction sites in the polylinker of pCIB2001 are EcoRI, SstI, Kpnf, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

An additional vector useful for Agrobacterium-mediated transformation is the binary vector pCIB10, which contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB10 have been constructed which incorporate the gene for hygromycin B phosphotransferase described by Gritz et al., *Gene* 25: 179–188 (1983). These derivatives enable selection of transgenic plant cells on hygromycin only (pCIB743), or hygromycin and kanamycin (pCEB715, pCIB717).

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., Nucl Acids Res 18: 1062 (1990), Spencer et al., *Theor Appl Genet* 79: 625–631(1990)), the hph gene which confers resistance to the antibiotic hygromycin (Blochinger & Diggelmann, *Mol Cell Biol* 4: 2929–2931), and the dhfr gene, which confers resistance to methotrexate (Bourouis et al., *EMBO J.* 2: 1099–1104 (1983)).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in the PCT published application WO 93/07278, herein incorporated by reference. One gene useful for conferring resistance to phosphinothricin is the bar gene from *Streptomyces viridochromogenes* (Thompson et al., *EMBO J* 6: 2519–2523 (1987)). This vector is suitable for the cloning of plant expression cassettes containing their own regulatory signals.

An additional transformation vector is pSOG35 which utilizes the E. coli gene dihydrofolate reductase (DHFR) as a selectable marker conferring resistance to methotrexate. PCR was used to amplify the 35S promoter (~800 bp), intron 6 from the maize Adh 1 gene (-550 bp) and 18 bp of the GUS untranslated leader sequence from pSOGIO. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOGl9 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus check (MCMV) generated the vector pSOG35. pSOG19 and pSOG35 carry the pUC-derived gene for ampicillin resistance and have HindII, SphI, PstI and EcoRI sites available for the cloning of foreign sequences.

Control of Plant Fertility

One of the advantageous aspects of the present invention is its use in the control of effective fertilization in plants under field conditions. Effective fertilization is the formation of viable zygotes. Plant fertility can be controlled by incorporating a nucleotide sequence encoding an appropriate target polypeptide into the target expression cassette wherein the expression of the target polypeptide which will render the fertilization process ineffective, meaning that the formation of viable zygotes will be prevented. Ineffective fertilization may be caused by a variety of means. These include but are not limited to, 1) disruption or alteration of those processes which are critical to formation of viable gametes, 2) pollen or ovules that, if formed, are not functional, or 3) failure of the embryo sac, pistil, stigma or transmitting tract to develop properly. In the present invention, a chemical ligand is applied to transgenic plants under field conditions, wherein the expression of a target polypeptide is activated, whereby fertilization is rendered ineffective.

Useful coding sequences for the target polypeptide include but are not limited to any sequence which encodes a product capable of rendering fertilization ineffective. These coding sequences can be of either a homologous or heterologous origin. The gene products of those coding sequences include, but are not limited to:

Diphtheria Toxin A-chain (DTA), which inhibits protein synthesis, Greenfield et al., *Proc. Natl. Acad., Sci.:USA*, 80:6853 (1983); Palmiter et al., *Cell*, 50:435 (1987);

Pectate lyase pelE from *Erwinia chrysanthemi* EC16, which degrades pectin, causing cell lysis. Keen et al., *J. Bacteriology*, 168:595 (1986);

T-urf13 (TURF-13) from cms-T maize mitochondrial genomes; this gene encodes a polypeptide designated URF13 which disrupts mitochondrial or plasma membranes. Braun et al., *Plant Cell*, 2:153 (1990); Dewey et al., *Proc. Natl. Acad. Sci.:USA*, 84:5374 (1987); Dewey et al., *Cell*, 44:439 (1986);

Gin recombinase from phage Mu a gene, which encodes a site-specific DNA recombinase which will cause genome rearrangements and loss of cell viability when expressed in cells of plants. Maeser et al., *Mol. Gen. Genet.*, 230:170–176 (1991);

Indole acetic acid-lysine synthetase (iaaL) from *Pseudomonas syringae*, which encodes an enzyme that conjugates lysine to indoleacetic acid (IAA). When expressed in the cells of plants, it causes altered developments due to the removal of IAA from the cell via conjugation. Romano et al., *Genes and Development*, 5:438–446 (1991); Spena et al., *Mol. Gen; Genet.*, 227:205–212 (1991); Roberto et al., *Proc. Natl. Acad. Sci.:USA*, 87:5795–5801;

Ribonuclease from *Bacillus amyloliquefaciens*, also known as barnase, digests mRNA in those cells in which it is expressed, leading to cell death. Mariani et al., *Nature* 347: 737–741 (1990); Mariani et al., *Nature* 357: 384–387 (1992); and, CytA toxin gene from *Bacillus thuringiensis israeliensis* which encodes a protein that is mosquitocidal and hemolytic. When expressed in plant cells, it causes death of the cell due to disruption of the cell membrane. McLean et al., *J. Bacteriology*, 169:1017–1023 (1987); Ellar et al., U.S. Pat. No. 4,918,006 (1990).

Such polypeptides also include Adenine Phosphoribosyltransferase (APRT) Moffatt and Somerville, Plant Physiol., 86:1150–1154 (1988); DNAse, RNAse; protease; salicylate hydroxylase; etc.

It is further recognized that the target expression cassette may comprise a 5' regulatory region operably linked to a nucleotide sequence which, when transcribed, produces an antisense version of a coding sequence critical to the formation of viable gametes, such as APRT. Alternately, ribozymes can be utilized which target mRNA from a gene which is critical to gamete formation or function. Such ribozymes will comprise a hybridizing region of about nine nucleotides which is complementary in nucleotide sequence to at least part of the target RNA and a catalytic region which is adapted to cleave the target RNA. Ribozymes are described in EPA No. 0 321 201 and WO88/04300 herein incorporated by reference. See, also Haseloff and Gerlach, *Nature*, 334:585–591 (1988); Fedor and Uhlenbeck, *Proc. Natl. Acad. Sci: USA*, 87:1668–1672 (1990); Cech and Bass, *Ann. Rev. Biochem.*, 55:599–629 (1986); Cech, T. R., 236:1532–1539 (1987); Cech, T. R. *Gene*, 73:259–271 (1988); and, Zang and Cech, *Science*, 231:470475 (1986).

It is recognized that the above nucleotide sequences encoding a target polypeptide can also be operably linked to a 5' regulatory sequence which directs its expression in a tissue- or cell-specific manner. The means to provide such tissue- or cell-specific expression has been described above. This specificity in expression ensures that the effect of the target polypeptide will be exerted only on those tissues or cells which are necessary for the formation of viable gametes and will not be deleterious to the plant beyond its affect on fertility.

It is recognized as within the scope of the invention that either male fertility of the transgenic plants, female fertility of the transgenic plants, or both, may be controlled. Male sterility is the failure or inability to produce functional or viable pollen. Male sterility may result from defects leading to the non-formation of pollen or to the lack of functional ability in the pollen when it is formed. Therefore, either pollen is not formed or, if formed, it is either non-viable or incapable of effective fertilization under normal conditions.

Female sterility is the failure or inability to produce functional or viable megaspores or embryo sacs, or other tissues required for pollen germination, growth or fertilization. Female sterility may result from defects leading to the non-formation of the megaspores or embryo sac, or failure of the ovary, ovule, pistil, stigma, or transmitting tract to develop properly. Therefore, either a viable embryo sac fails to develop, or if formed, it is incapable of effective fertilization under normal conditions.

For example, a transgenic plant can be obtained which expresses the EcR and USP receptor polypeptides in anthers using an anther-specific promoter fused to the appropriate nucleotide sequences. In addition, the transgenic plant will further comprise a target expression cassette having a 5' regulatory sequence comprising the appropriate response element sequence with the core promoter elements from Bz1, operably linked to the coding sequence for the ribonuclease barnase. Upon application of RH 5992 as chemical ligand to the transgenic plant, heterodimerization of the EcR and USP receptor polypeptides occurs, activating the 5' regulatory sequence of the target expression cassette and with subsequent production of the target polypeptide barnase. The resulting expression of barnase specifically in the anthers causes cell death and consequent male sterility. A similar combination of receptor polypeptides and target expression cassette, using a pistil-specific promoter operably linked to the nucleotide sequences encoding the receptor polypeptides, can produce female sterility.

Alternatively, the plant could be engineered wherein expression of the target polypeptide restores fertility to a male-sterile or female-sterile plant. For example, a plant could be obtained that expressed the barnase gene under control of the Ant43D, Ant32 or B6 promoters, or as described in Mariani et al., *Nature* 347: 737–741 (1990) and Mariani et al., *Nature* 357: 384–387 (1992), under control of the TA29 promoter. These plants would additionally comprise the receptor expression cassettes which express the EcR and USP receptor polypeptide from either the same anther-specific promoter or from a constitutive promoter such as maize ubiquitin, 35S or rice actin. These plants would further comprise a target expression cassette having a 5' regulatory sequence comprising the appropriate response element sequence with the core promoter elements from Bz1, operably linked to the coding sequence for the barnase inhibitor barstar. The plants would be male-sterile, but upon application of RH5992 as a chemical ligand, heterodimerization of USP and EcR receptor polypeptides would occur, resulting in activation of the 5' regulatory sequence of the target expression cassette and production of the target polypeptide barstar. Barstar would inhibit the ribonuclease activity of the barnase polypeptide, and anther and pollen development would proceed normally. Fertility would be restored.

A similar approach could be used to control female sterility. By utilizing promoters specific for expression in the female reproductive tissues to drive barnase expression instead of the anther-specific promoters, female-sterile plants would be obtained. Induction by chemical ligand of the target expression cassette comprising the barstar coding sequence would result in restoration of female fertility.

The above approaches could utilize any female- or male-sterility gene for which a restorer gene could be devised. Other potential restorer genes are described in European Patent Application EP 412 911.

Therefore, the present invention can be used in any plant which can be transformed and regenerated to obtain transgenic plants in which male and/or female sterility can be controlled by the application of the appropriate chemical ligand. The control of plant fertility is particularly useful for the production of hybrid seed. In order to produce hybrid seed uncontaminated with selfed seed, pollination control methods must be implemented to ensure cross-pollination and not self-pollination. This is usually accomplished by mechanical, genetic or chemical hybridizing agents (CHAs). For example, in maize the current practice is mechanical detasseling of the female (or seed) parent, which is a time consuming and labor intensive process. In wheat, controlling fertility by mechanical means is impractical on a seed production scale, and genetic sources of control are not established. The use of the present invention in the production of hybrid seed offers the advantages of reliability, ease of use and control of either male or female fertility.

The transgenic plants containing the appropriate receptor expression cassettes and target expression cassette can be made homozygous and maintained indefinitely. To obtain hybrid seed, homozygous lines of Parent 1 and Parent 2 are crossed. In one example of using the present invention to produce hybrid seed, Parent 1 is engineered to be male sterile in the presence of the appropriate chemical ligand whereas Parent 2 is engineered to be female sterile in the presence of an appropriate chemical ligand. After application of an appropriate chemical ligand, which is determined by the choice of ligand binding domain present in the receptor polypeptides, the only successful seed production will be a result of Parent 2 pollen fertilizing Parent I ovules. In a second example of using the present invention, Parent 1 is engineered to be male-sterile in the absence of the appropriate chemical ligand and Parent 2 is engineered to be female sterile in the absence of the chemical ligand. The appropriate chemical is applied to maintain each line through self-fertilization. To produce hybrid seed, the two parent lines are interplanted, and only hybrid seed is obtained. Fertility is restored to the progeny hybrid plants by an introduced restorer gene. By these means any desired hybrid seed may be produced.

EXAMPLES

The following examples further describe the materials and methods used in carrying out the invention and the subsequent results. They are offered by way of illustration, and their recitation should not be considered as a limitation of the claimed invention.

Example 1
Construction of a Plant-Expressible Receptor Expression Cassette Encoding the Ecdysone Receptor The DNA coding region for the Ecdysone Receptor (EcR) of Drosophila was isolated from a cDNA library derived from Canton S pupae (day 6) prepared in λgt11 (Clontech, cat. no. IL 1005b), and from fragments generated by genomic PCR with oligonucleotides designed from the published sequence of the B1 isoform of the EcR (Koelle et al., *Cell* 67:59, 1991). The B1 isoform EcR sequence was confirmed by automated sequence analysis using standard methods and alignment with the published sequence (Talbot et al., *Cell* 73:1323, 1993). The expressed full length EcR coding region was modified to contain a BamHI site immediately upstream from the start codon using the oligonucleotide SF43 (5'-CGC GGA TCC TAA ACA ATG AAG CGG CGC TGG TCG AAC AAC GGC-3'; SEQ ID NO: 1) in a PCR reaction. The plant expression vectors pMF6 and pMF7 contain a Cauliflower Mosaic Virus 35S promoter (CaMV 35S), a maize Adh1 Intron1, and a nopaline synthetase polyadenylation and termination signal (See Goff et al., *Genes and Development* 5:298, 1991). The vectors pMF6 and pMF7 differ only in the orientation of the polylinker used for insertion of the desired coding sequence. The full length EcR coding sequence was ligated into the plant CaMV 35S expression vector pMF6 by using the flanking BamHI restriction sites. This receptor expression cassette is referred to as 35S/EcR.

Example 2
Construction of a Plant-Expressible Receptor Expression Cassette Encoding the Ultraspiracle Receptor The cDNA encoding the native Ultraspiracle receptor (USP) of Drosophila is described by Henrich et al., *Nucleic Acids Research* 18:4143 (1990). The full length USP coding sequence with the flanking 5' and 3' untranslated regions was ligated into the plant expression vector pMF7 (described in Example 1) using the flanking EcoRI restriction sites. This receptor expression cassette is referred to as 35S/USP.

Example 3
Construction of a Receptor Expression Cassette having the DNA Binding Domain from GAL4 and the Ligand Binding Domain from EcR A receptor expression cassette was constructed where the DNA binding domain of EcR is replaced by the DNA binding domain of GAL4 fused at the N-terminal position. The DNA coding region for the EcR of Drosophila was obtained as described in Example 1. The coding sequence for the DNA binding domain of GAL4 was subcloned from plasmid pMA210. Ma and Ptashne, *Cell,* 48: 847 (1987).

A receptor expression cassette encoding a GAL4-EcR chimeric receptor polypeptide was constructed by fusion of the DNA binding domain of GAL4 to the ligand binding domain and carboxy terminus of EcR. To make the fusion, the oligonucleotide SF23 (5'-CGC GGG ATC CAT GCG GCC GGA ATG CGT CGT CCC G-3'; SEQ ID NO:2) was used to introduce by PCR a BamHI site into the cDNA sequence for EcR at the nucleotide position equivalent to amino acid residue 330 (immediately following the EcR DNA-binding domain). The resulting truncated EcR coding sequence (EcR$^{330-878}$) was subcloned into the plasmid pKS+ (Stratagene).

A subclone of GAL4 was obtained from plasmid pMA210 which contained the coding sequence of the DNA binding domain (amino acids 1–147) by subcloning the amino terminus of GAL4 to the ClaI site into pSK+(Stratagene) as previously described (Goff et al., Genes and Development 5:298, 1991). This plasmid was designated pSKGAL2, and was cut with ClaI and KpnI and the following double stranded oligonucleotide was inserted:

5'-CGGGGGATCCTAAGTAAGTAAGGTAC-3'(SEQ ID NO: 10)

3'-CCCCTAGGATTCATTCATTC-5' (SEQ ID NO:11)

The resulting plasmid was designated pSKGAL2.3. The complete fusion 35S/GAL4-EcR$^{330-878}$ was generated using the BamHI sites in the polylinkers flanking the DNA binding domain of GAL4 in pSK+ and the EcR$^{330-878}$ moiety in pKS+. These coding sequences were ligated into the monocot expression vector pMF6 (described in Example 1) via the use of the flanking EcoRI restriction sites. This receptor expression cassette is referred to as 35S/GAL4-EcR$^{330-878}$.

Example 4

Construction of a Plant-Expressible Receptor Expression Cassette having the Ligand Binding Domain from Ultraspiracle and the Transactivation Domain from VP16

A receptor expression cassette was constructed which comprises the ligand binding domain of USP with the transactivation domain of VP16 fused to either the N-terminus or C-terminus of the USP polypeptide.

To construct the receptor expression cassette encoding a chimeric polypeptide having the transactivation domain of VP16 at the C-terminal position, the carboxy-terminus and stop codon of the cDNA for the receptor USP (described in Example 2) were removed by subcloning into pKS+ (Stratagene) using the XhoI site at USP nucleotide number 1471 of the coding sequence. The resulting USP subclone encoding amino acids 1 to 490 was fused to the transactivation domain of VP16 using the flanking KpnI restriction site of the USP subclone, and the KpnI site of PSJT 1193CRF3 which encodes the carboxy-terminal 80 amino acids of VP 16 (Triezenberg et al., Genes and Develop. 2: 718–729 (1988)). The resulting USP-VP16 fusion was cloned into the CaMV 35S plant expression vector pMF7 (described in Example 1) using the EcoRI and BamHI restriction enzyme sites flanking the coding sequence of USP-VP16. This receptor expression cassette is referred to as 35S/USP-VP16.

The USP derivative with the transcriptional activation domain fused to the amino-terminus was constructed by first engineering a BamHI site adjacent to the USP start codon using the oligonucleotide SF42 (5'-CGC GGA TCC ATG GAC AAC TGC GAC CAG GAC-3'; SEQ ID NO:3) in a PCR reaction. The stop codon in VP16 was eliminated and a flanking BamHI site introduced using the oligonucleotide SF37 (5'-GCG GGA TCC CCC ACC GTA CTC GTC AAT TC-3'; SEQ ID NO:4) and a start codon with a plant consensus sequence as well as a BamHI site was introduced at the amino terminal end using the oligonucleotide SA115 (5'-GTC GAG CTC TCG GAT CCT AAA ACA ATG GCC CCC CCG ACC GAT GTC-3'; SEQ ID NO:5) as primers in a PCR reaction. The resulting VP16 activation domain and USP coding-sequence (encoding amino acids 1 to 507) were joined in frame by the adjacent BamHI sites, and the VP16-USP coding sequence was inserted into the CaMV 35S plant expression vector pMF7 by the 5' BamHI and 3' EcoRI sites. This receptor expression cassette is referred to as 35SNVP16-USP.

Example 5

Construction of a Receptor Expression Cassette Having the DNA Binding Domain and Ligand Binding Domain from EcR and the Transactivation Domain from the Cl Regulatory Gene of Maize The EcR$^{227-825}$-C1 fusion was generated by placing a start codon immediately before the EcR DNA binding domain with the oligonucleotide SF30 (5'-CGC-GGA-TCC-ATG-GGT-CGC-GAT-GAT-CTC-TCG-CCT-TC-3'; SEQ ID NO: 8) used in a PCR reaction on the full length EcR coding sequence. The coding sequence for the transcriptional activation domain (amino acids 219–273) of the maize C1 protein (Goff et al. Genes and Develop. 5: 298–309 (1991)) was fused in frame to the coding sequence for amino acids 51 to 825 of EcR (at the EcR KpnI restriction enzyme site). The C1 transactivation domain was linked to EcR by a polylinker encoding VPGPPSRSRVSISLHA (SEQ ID NO:9). The 35S/EcR$^{227-525}$-C1 plant expression vector fusion was constructed by insertion of a BamHI fragment carrying the coding sequence into the pMF7 vector. This receptor expression cassette is referred to as 35S/EcR$^{227-825}$-C1.

Example 6

Construction of a Receptor Expression Cassette Having the DNA Binding Domain from GAL4, the Ligand Binding Domain from EcR and the Transactivation Domain from the C1 Regulatory Gene of Maize A GAL4-EcR$^{330-825}$-C1 fusion was constructed using the GAL4-EcR$^{330-878}$ construct described in Example 3 and the EcR$^{227-825}$-C1 construct of Example 5. The sequence of the EcR coding region (at amino acid 456) was exchanged at the AatII site. This receptor expression cassette is referred to as 35S/GAL4-EcR$^{330-825}$-C1.

Example 7

Construction of a Plant-Expressible Target Expression Cassette Encoding Firefly Luciferase having the Response Element for the GAL4 DNA Binding Domain The plant-expressible target expression cassette encoding firefly luciferase having the response element for the DNA binding domain of GAL4 was constructed in the following manner. The maize Bronze-1 (Bz1) core promoter driving the synthesis of firefly luciferase was removed from the Bz1 reporter pBz1LucR98 (Roth et al., Plant Cell 3:317, 1991) via the NheI and SphI sites and placed in a pUC6S-derived plasmid carrying the luciferase gene. The modified Bz1 core promoter contains an NheI site (GCTAGC) and Bz1 promoter sequences up to nucleotide position −53 (Roth et al., Plant Cell 3:317, 1991). Ten GAL4 binding sites were removed from the GAL4 regulated reporter pGALLuc2 (Goff et al., Genes and Development 5:298, 1991) by digestion with EcoRI and PstI and inserted into pBlueScript (Stratagene) using the same restriction enzyme sites. The HindIII site at the 5' end of the GAL4 binding sites was changed to a BamHI site by insertion of an HindIII/BamHI/HindIII adaptor, and the resulting BamHI fragment containing the GAL4 binding sites was removed and placed into a BgM site upstream of the Bz1 core promoter driving luciferase. This target expression cassette is referred to as (GAL4$_{b.s.}$)$_{10}$-Bz1$_{TATA}$/Luc.

Example 8
Construction of a Plant-Expressible Target Expression Cassette Encoding Firefly Luciferase Having the Response Element for EcR DNA Binding Domain The plant-expressible target expression cassette encoding firefly luciferase having the response element for the DNA binding domain of EcR was constructed in the following manner. The maize Bz1 core promoter-luciferase construct in the pUC6S-derived plasmid as described in Example 7 was used as the starting point. Double-stranded synthetic oligonucleotides containing the Drosophila hsp27 response element which complements the DNA binding domain of EcR were constructed with BamHI and Bgm cohesive ends (SF25: 5'-GAT CCG ACA AGG GTT CAA TGC ACT TGT CA-3'; SEQ ID NO:6) (SF26: 5'-GAT CTG ACA AGT GCA TTG AAC CCT TGT CG-3'; SEQ ID NO:7), phosphorylated, and ligated upstream of the Bz1 core promoter by insertion into a unique Bgm site. Multiple copies of the response element were obtained by sequential Bgm digestion and insertion of additional double-stranded oligonucleotides. This target expression cassette is referred to as either (EcRE)$_5$-Bz1/Luc, (EcRE)$_6$-Bz1/Luc, or (EcRE)$_8$-Bz1/Luc, depending on the number of full-site palindromic response elements contained within the promoter region (5, 6, and 8, respectively).

Example 9
Transformation of Plant Cells and Control of Target Polypeptide Expression by Receptor Polypeptides in the Presence of a Chemical Ligand Control of target polypeptide expression by various receptor polypeptides, including the chimeric receptor polypeptides of the present invention, can be shown by simultaneously transforming plant cells with the necessary gene constructions using high velocity microprojectile bombardment, followed by biochemical assay for the presence of the target polypeptide. The necessary gene constructions comprise a first receptor expression cassette which encodes a first receptor polypeptide and a second receptor expression cassette which encodes a second receptor polypeptide. In addition, a target expression cassette which encodes a target polypeptide is also necessary (FIG. 1).

The expression cassettes were simultaneously delivered to maize suspension cells cultured in liquid N6 medium (Chu et al. *Scientia Sinica XVIII*:659–668, 1975) by high velocity microprojectile bombardment using standard techniques of DNA precipitation onto microprojectiles and high velocity bombardment driven by compressed helium (PDS-1000/He, BioRad, Hercules, Calif.). Transfected cells were incubated in liquid suspension in the presence of the appropriate chemical ligand for approximately 48 hours in N6 media After incubation, the transformed cells were harvested then homogenized at 0° C. Debris in the extracts was removed by centrifugation at 10,000 g at 4° C. for 5 minutes.

Target polypeptide expression was detected by assaying the extract for the presence of the product encoded by the target expression cassette. One commonly used coding sequence for the target polypeptide when testing control of expression by the receptor polypeptides in the presence of a chemical ligand is firefly luciferase. The activity of firefly luciferase is determined by quantitating the chemiluminescence produced by luciferase catalyzed phosphorylation of luciferin using ATP as substrate (Promega Luciferase Kit, cat. no. E1500), using an Analytical Luminescence Model 2001 luminometer.

Figure 2:
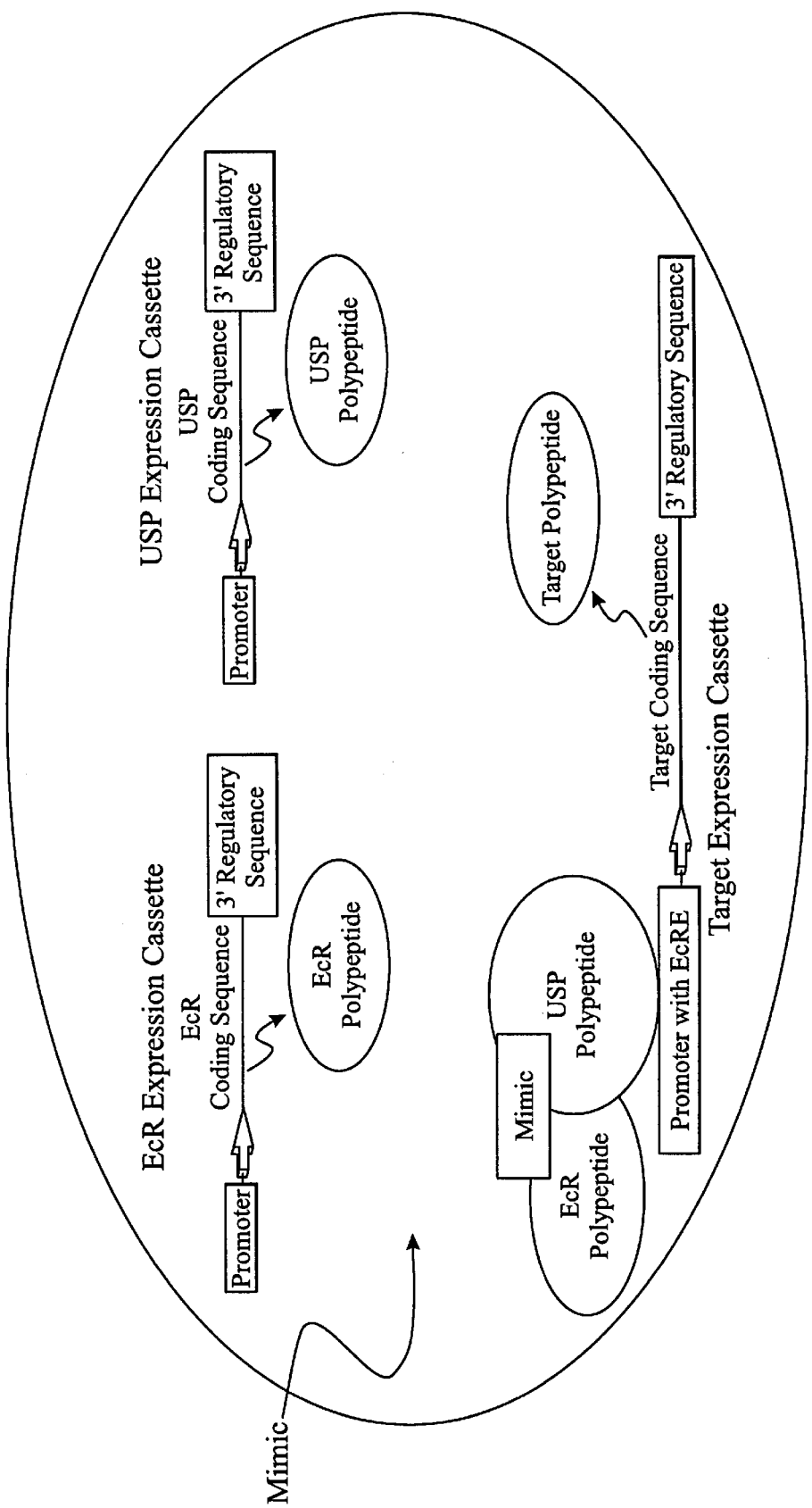
FIG. 2. Same as FIG. 1, except the first receptor polypeptide is the Ecdysone Receptor (EcR), the second receptor polypeptide is Ultraspiracle (USP), and the chemical ligand is MIMIC®.

Example 10
The Receptor Polypeptides EcR and USP Activate Expression of a Target Polypeptide in Plant Cells Using the transformation method of Example 9, the receptor expression cassette 35S/EcR (Example 1), the receptor expression cassette 35S/USP (Example 2) and the target expression cassette (EcRE)$_5$-Bz1/Luc (Example 8) were co-transformed into maize cells (see FIG. 2). Transformed cells were incubated in the presence of 10 µM RH5992 or 2 µM muristerone as chemical ligands for approximately 48 hours. Luciferase assays were performed as described in Example 9. The results are presented in Table 1.

TABLE 1

| Receptor | Presence of Chemical Ligand | Luciferase Activity (light units) |
| --- | --- | --- |
| None | None | 427 |
| 35S/EcR | None | 295 |
| 35S/EcR + 35S/USP | RH5992 | 860 |
| 35S/EcR + 35S/USP | Muristerone | 1351 |

The above results show that the 5' regulatory region of the target expression cassette comprising the EcR response elements can be activated in plant cells by the receptor polypeptides EcR and USP in the presence of a complementary chemical ligand. The level of expression of the target polypeptide luciferase was about 2- to 3-fold above that observed in the absence of chemical ligand.

Example 11
The Receptor Polypeptides VP16-USP and EcR Activate Expression of a Target Polypeptide in Plant Cells Using the transformation method of Example 9, the receptor expression cassette 35S/EcR (Example 1), the receptor expression cassette 35S/VP16-USP (Example 4) and the target expression cassette (EcRE)$_6$-Bz1/Luc (Example 8) were co-transformed into maize cells. Transformed cells were incubated in the presence of 1 µM ecdysone, 10 µM RH5992 or 2 µM muristerone as chemical ligands for 48 hours. Luciferase assays were performed as described in Example 9. The results are presented in Table 2.

TABLE 2

| Receptor | Presence of Chemical Ligand | Luciferase Activity (light units) |
| --- | --- | --- |
| None | None | 427 |
| 35S/EcR + 35S/VP16-USP | None | 4,486 |
| 35S/EcR + 35S/VP16-USP | ecdysone | 7,420 |
| 35S/EcR + 35S/VP16-USP | RH5992 | 7,003 |
| 35S/EcR + 35S/VP16-USP | Muristerone | 12,374 |

The above results show that the 5' regulatory region of the target expression cassette comprising the EcR response elements can be activated in plant cells by the receptor polypeptide EcR and the chimeric receptor polypeptide VP16-USP in the presence of a complementary chemical ligand. The level of expression of the target polypeptide luciferase was about 2- to 3-fold above that observed in the absence of chemical ligand.

Example 12
The Receptor Polypeptides EcR$^{227-825}$-C1 and USP Activate Expression of a Target Polypeptide in Plant Cells Using the transformation method of Example 9, the receptor expression cassette 35S/USP (Example 2), the receptor expression cassette 35S/EcR$^{227-825}$-C1 (Example 5) and the target expression cassette (EcRE)$_6$-Bz1/Luc (Example 8) were co-transformed into maize cells. Transformed cells were incubated in the presence of 10 μM RH5992 as chemical ligand for 48 hours. Luciferase assays were performed as described in Example 9. The results are presented in Table 3.

TABLE 3

| Receptor | Presence of Chemical Ligand | Luciferase Activity (light units) |
|---|---|---|
| None | None | 5,626 |
| 35S/USP + 35S/EcR$^{227-825}$-C1 | None | 10,024 |
| 35S/USP + 35S/EcR$^{227-825}$-C1 | RH5992 | 24,631 |

The above results show that the 5' regulatory region of the target expression cassette comprising the EcR response elements can be activated in plant cells by the receptor polypeptide USP and the chimeric receptor polypeptide EcR$^{227-825}$-C1 in the presence of a complementary chemical ligand. The chimeric receptor polypeptide uses the transactivation domain of the maize regulatory gene C1 fused to the C-terminus of a truncated EcR, where the truncation has removed the transactivation domain of EcR. The level of expression of the target polypeptide luciferase was more than 2-fold above that observed in the absence of chemical ligand.

Figure 3:
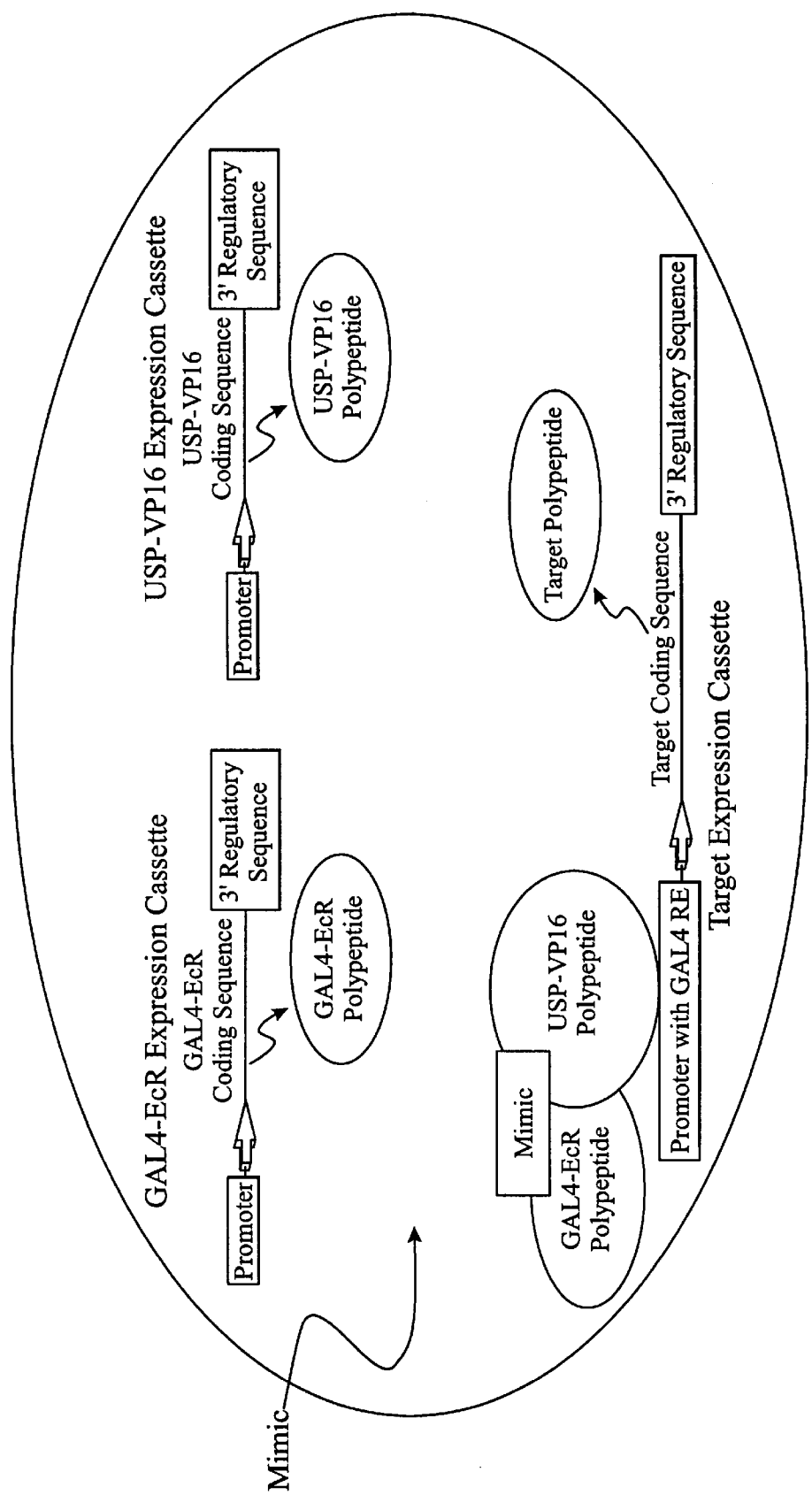
FIG. 3. Same as FIG. 1, except the first receptor polypeptide is a GAL4-EcR fusion, the second receptor polypeptide is a USP-VP16 fusion, and the chemical ligand is MIMIC®.

Example 13
Activation of a Target Expression Cassette in Plant Cells is Enhanced by Using a Chimeric Receptor Polypeptide Having a Strong Transactivation Domain Using the transformation method of Example 9, the receptor expression cassette 35S/GAL4-EcR$^{330-878}$ (Example 3), the receptor expression cassette 35S/USP-VP16 (Example 4) and the target expression cassette (GAL4)$_{10}$-Bz1/Luc (Example 7) were co-transformed into maize cells (FIG. 3). Transformed cells were incubated in the presence of 10 μLM RH5992 as chemical ligand for approximately 48 hours. Luciferase assays were performed as described in Example 9. The results are presented in Table 4.

TABLE 4

| Chimeric Receptor | Presence of RH5992 | Luciferase Activity (light units) |
|---|---|---|
| 35S/GAL4-EcR$^{330-878}$ | – | 2,804 |
| 35S/USP-VP16 | – | 6,121 |
| 35S/GAL4-EcR$^{330-878}$ + 35S/USP-VP16 | – | 3,586 |
| 35S/GAL4-EcR$^{330-878}$ + 35S/USP-VP16 | + | 130,601 |

The above results show that the 5' regulatory region of the target expression cassette comprising the GAL4 response elements can be activated in plant cells by the receptor polypeptides GAL4-EcR$^{330-878}$ and USP-VP16 in the presence of a complementary chemical ligand. The level of expression of the target polypeptide luciferase was 36-fold above that observed in the absence of chemical ligand. This indicates 1) that the chimeric receptor polypeptide bound to the GAL4 response elements of the target expression cassette, 2) that RH5992 bound to the ligand binding domain of the EcR$^{330-878}$ moiety in the chimeric receptor polypeptide, 3) that the two chimeric receptor polypeptides properly heterodimerized, and 4) that the heterodimerization brought the transactivation domain from VP16 into position for activation.

Example 14
A Transactivation Domain Can be Used on Each Chimeric Receptor Polypeptide Using the transformation method of Example 9, the receptor expression cassette 35S/GAL4-EcR$^{330-825}$-C1 (Example 6), the receptor expression cassettes 35S/USP-VP16 or 35S/VP16-USP (Example 4) and the target expression cassette (GAL4)$_{10}$-Bz1/Luc (Example 7) were co-transformed into maize cells. Transformed cells were incubated in the presence of 10 μM RH5992 as chemical ligand for approximately 48 hours. Luciferase assays were perfomed as described in Example 9. The results are presented in Table 5.

TABLE 5

| Chimeric Receptor | Presence of RH5992 | Luciferase Activity (light units) |
|---|---|---|
| 35S/GAL4-EcR$^{330-825}$-C1 + 35S/VP16-USP | – | 3,423 |
| 35S/GAL4-EcR$^{330-825}$-C1 + 35S/VP16-USP | + | 11,069 |
| 35S/GAL4-EcR$^{330-825}$-C1 + 35S/USP-VP16 | – | 5,972 |
| 35S/GAL4-EcR$^{330-825}$-C1 + 35S/USP-VP16 | + | 37,579 |

The above results show that the 5' regulatory region of the target expression cassette (GAL4)$_{10}$-Bz1/Luc comprising the GAL4 response elements can be activated in plant cells by the receptor polypeptides 35S/GAL4-EcR$^{330-825}$-C1 and 35S/VP16-USP or 35S/USP-VP 16 in the presence of a complementary chemical ligand. The expression of the target polypeptide was greater (6-fold over the absence of ligand) with VP-16 fused to the C-terminal end of USP compared to fusion of VP-16 to the N-terminal end (only a 3-fold enhancement).

Example 15
Isolation of Receptor Polypeptide Mutants having Lowered Basal Activity Mutations in the ligand binding domain of both the ecdysone receptor (EcR) or the Ultraspiracle receptor (USP) were generated in vitro using PCR mutagenesis as described by Leung et al., *Technique* 1: 11–15 (1989). PCR fragments of mutated EcR ligand binding domain were cloned into a yeast expression vector as a fusion with the DNA binding domain of yeast GAL4. PCR fragments of mutated USP ligand binding domain were cloned into a yeast expression vector as a fusion with the transcriptional activation domain of VP16. Mutant constructs were transformed into the yeast GAL4 reporter strain GGY1::171. The mutant GAL4-EcR constructs were transformed in combination with non-mutagenized VP16-USP, and mutant USP-VP16 constructs were transformed in combination with non-mutagenized GAL4-EcR$^{330-825}$-C1. Yeast transformants were plated on media containing the indicator X-Gal. Mutants having a decreased basal level of receptor polypeptide activity for the heterodimer generated white to light blue colonies on X-Gal indicator plates, while the non-mutagenized receptor polypeptide heterodimers generated dark blue colonies. White to light blue colonies are tested for the basal and chemical ligand-induced level of receptor polypeptide activity by growing yeast cells representing those selected colonies in S media containing glycerol, ethanol and galactose as carbon sources. The resulting culture is split into two portions, one of which is treated with an appropriate chemical ligand and the other is used as a control in the absence of chemical ligand. After exposure to the chemical ligand, both the treated and control portions of the culture are assayed for β-galactosidase activity according to the procedure of Miller (*Experiments in Molecular Genetics*, p. 352–355, J. H. Miller, Ed., Cold Spring Harbor Laboratory, Cold Spring Harbor, N.Y., 1972). The nucleotide sequences which encode the mutant receptor polypeptides isolated and identified by this technique are candidates for further testing since they may exhibit, in plant cells, a decreased basal activity and a greater fold induction of target gene expression in the presence of the chemical ligand.

Example 16
Identification of Mutant Receptor Polypeptides with Improved Function in Plant Cells Receptor expression cassettes which encode the mutated EcR or USP receptor polypeptides of Example 15 are prepared according to the above Examples 1 through 6. These receptor expression cassettes, in combination with one of the target expression cassettes of Examples 7 and 8, are transformed into plant cells according to the procedure of Example 9. Transformed plant cells are tested for activation of the 5'-regulatory region of the target expression cassette by the mutant receptor polypeptides in the presence of an appropriate chemical ligand. Mutant EcR or USP receptor polypeptides which produce, in plant cells, low basal expression of a target polypeptide in the absence of chemical ligand and high expression of target polypeptide in the presence of an appropriate chemical ligand are useful for controlling gene expression in plants.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of controlling the fertility of a plant comprising:
   a) transforming said plant with a first receptor expression cassette which encodes a first receptor polypeptide comprising a first ligand binding domain and a first DNA binding domain; a second receptor expression cassette which encodes a second receptor polypeptide comprising a second ligand binding domain and a second DNA binding domain, wherein said first and second receptor polypeptides are members of the Class II steroid and thyroid hormone superfamily of nuclear receptors; and a target expression cassette comprising a 5' regulatory region operably linked to a nucleotide sequence encoding a target polypeptide that renders fertilization ineffective or restores effective fertilization, wherein said 5' regulatory region comprises one or more response elements complementary to said first or second DNA binding domain;
   b) expressing said first and second receptor polypeptides in said transformed plant; and
   c) contacting said transformed plant with one or more chemical ligands which are complementary to the ligand binding domain of said first or second receptor polypeptides whereby said receptor polypeptides in the presence of said chemical ligand activate the expression of said target polypeptide, wherein said target polypeptide renders fertilization ineffective or restores effective fertilization.

2. The method of claim 1 wherein said first receptor expression cassette comprises an anther-specific promoter operably linked to the coding sequence for said first receptor polypeptide, said second receptor expression cassette comprises an anther-specific promoter operably linked to the coding sequence for said second receptor polypeptide, or both said first and said second receptor expression cassettes comprise an anther-specific promoter operably linked to the coding sequence for said first and second receptor polypeptides.

3. The method of claim 1 wherein said first receptor expression cassette comprises a pistil-specific promoter operably linked to the coding sequence for said first receptor polypeptide, said second receptor expression cassette comprises a Pistil-specific promoter operably linked to the coding sequence for said second receptor polypeptide, or both said first and said second receptor expression cassettes comprise a pistil-specific promoter operably linked to the coding sequence for said first and second receptor polypeptides.

4. The method of claim 1 wherein said target polypeptide renders fertilization ineffective.

5. The method of claim 4 wherein said target polypeptide is the ribonuclease barnase.

6. The method of claim 1 wherein said target polypeptide restores effective fertilization.

7. The method of claim 6 wherein said target polypeptide is the ribonuclease inhibitor barstar.

8. The method of claim 1 wherein said first receptor polypeptide is Ecdysone Receptor.

9. The method of claim 8 wherein said first receptor polypeptide further comprises a heterologous transactivation domain.

10. The method of claim 9 wherein said heterologous transactivation domain is the transactivation domain from the C1 regulatory gene of maize.

11. The method of claim 8 wherein said first DNA binding domain is heterologous with respect to said first receptor polypeptide.

12. The method of claim 11 wherein said first DNA binding domain is the DNA binding domain from the GAL4 protein of yeast.

13. The method of claim 1 wherein said second receptor polypeptide is USP.

14. The method of claim 13 wherein said second receptor polypeptide further comprises a heterologous transactivation domain.

15. The method of claim 14 wherein said heterologous transactivation domain is the transactivation domain from the VP16 protein of herpes simplex.

16. The method of claim 12 wherein said first receptor polypeptide further comprises a heterologous transactivation domain from the C1 regulatory gene of maize.

17. The method of claim 1 wherein said chemical ligand is an insect hormone, an insect hormone antagonist or an insect hormone agonist.

18. The method of claim 17 wherein said chemical ligand is fenoxycarb; CGA 59,205; RH 5992;

or RH 5849.

19. The method of claim 1 wherein said 5' regulatory region of said target expression cassette comprises between 1 and 11 response element copies.

20. The method of claim 1 wherein said first receptor polypeptide further comprises a heterologous transactivation domain.

21. The method of claim 1 wherein said second receptor polypeptide further comprises a heterologous transactivation domain.

22. The method of claim 1 wherein said first receptor polypeptide further comprises a heterologous transactivation domain and wherein said second receptor polypeptide further comprises a heterologous transactivation domain.

23. The method of claim 1 wherein said first DNA binding domain is heterologous with respect to said first receptor polypeptide.

24. The method of claim 1 wherein said second DNA binding domain is heterologous with respect to said first receptor polypeptide.

25. The method of claim 1 wherein said first DNA binding domain is heterologous with respect to said first receptor polypeptide and wherein said second DNA binding domain is heterologous with respect to said first receptor polypeptide.

26. The method of claim 8 wherein said 5' regulatory region comprises one or more response elements complementary to the DNA binding domain of Ecdysone Receptor.

27. The method of claim 26 wherein said second receptor polypeptide is USP.

28. The method of claim 27 wherein said second receptor polypeptide further comprises a heterologous transactivation domain from the VP16 protein of herpes simplex.

29. The method of claim 27 wherein said first receptor polypeptide further comprises a heterologous transactivation domain from the C1 regulatory gene of maize.

30. The method of claim 12 wherein said 5' regulatory region comprises one or more response elements complementary to the DNA binding domain from the GAL4 protein of yeast.

31. The method of claim 30 wherein said second receptor polypeptide is USP and wherein said second receptor polypeptide further comprises a heterologous transactivation domain from the VP16 protein of herpes simplex.

32. The method of claim 30 wherein said first receptor polypeptide further comprises a heterologous transactivation domain from the C1 regulatory gene of maize, wherein said second receptor polypeptide is USP, and wherein said second receptor polypeptide further comprises a heterologous transactivation domain from the VP16 protein of herpes simplex.

33. A method of controlling the fertility of a plant comprising:
   a) transforming said plant with a first receptor expression cassette which encodes a first receptor polypeptide comprising a first ligand binding domain and a first DNA binding domain; a second receptor expression cassette which encodes a second receptor polypeptide comprising a second ligand binding domain and a second DNA binding domain, wherein said first and second receptor polypeptides are members of the Class II steroid and thyroid hormone superfamily of nuclear receptors; and a target expression cassette comprising a 5' regulatory region operably linked to a nucleotide sequence encoding the anti-sense version of a coding sequence critical to effective fertilization, wherein said 5' regulatory region comprises one or more response elements complementary to said first or second DNA binding domain;
   b) expressing said first and second receptor polypeptides in said transformed plant; and
   c) contacting said transformed plant with one or more chemical ligands which are complementary to the ligand binding domain of said first or second receptor polypeptides whereby said receptor polypeptides in the presence of said chemical ligand activate the expression of said anti-sense sequence, wherein said anti-sense sequence renders fertilization ineffective.

* * * * *